United States Patent [19]

Takashima et al.

[11] Patent Number: 5,277,057
[45] Date of Patent: Jan. 11, 1994

[54] GASOLINE DETECTING DEVICE

[75] Inventors: Hiromasa Takashima; Kazutoshi Angata, both of Shizuoka; Takamitsu Ariyoshi; Hiromi Sonoda, both of Aichi, all of Japan

[73] Assignee: Yazaki Corporation, Japan

[21] Appl. No.: 925,172

[22] Filed: Aug. 6, 1992

[51] Int. Cl.⁵ .................... G01N 33/22; G01M 3/16
[52] U.S. Cl. ...................... 73/31.01; 73/40.7
[58] Field of Search .............. 73/31.01, 31.02, 40.7, 73/40.5

[56] References Cited

U.S. PATENT DOCUMENTS

| 2,346,043 | 4/1944 | Mysels | 73/40.7 X |
| 2,947,166 | 8/1960 | Palmer et al. | 73/40.7 |
| 3,302,449 | 2/1967 | Roberts | 73/40.7 |
| 3,343,402 | 9/1967 | Hubner | 73/31.02 |
| 3,375,700 | 4/1968 | Hubner | 73/31.02 |
| 3,786,675 | 1/1974 | Delatorre et al. | 73/40.7 X |
| 4,173,886 | 11/1979 | Archbold et al. | 73/31.02 |
| 4,369,647 | 1/1983 | Shigemori et al. | 73/25.03 |
| 4,785,658 | 11/1988 | Jackson | 73/31.01 |
| 4,786,472 | 11/1988 | McConnell et al. | 73/31.01 X |
| 4,879,546 | 11/1989 | Dunham et al. | 73/31.02 X |

FOREIGN PATENT DOCUMENTS 2072852 10/1981 United Kingdom .

*Primary Examiner*—Tom Noland
*Assistant Examiner*—Joseph W. Roskos
*Attorney, Agent, or Firm*—Wigman, Cohen, Leitner & Myers

[57] ABSTRACT

A gasoline detecting device is provided with a suction nozzle arranged adjacent to an element to be inspected, a sensor for detecting gasoline within the sucked air arranged adjacent to the suction nozzle, and a body arranged in relation spaced from the suction nozzle. The body has a sensor drive unit for driving the sensor and for displaying the detection and a suction unit communicating with the suction nozzle. The gasoline detecting device can detect gasoline leakage from the element to be inspected.

3 Claims, 4 Drawing Sheets

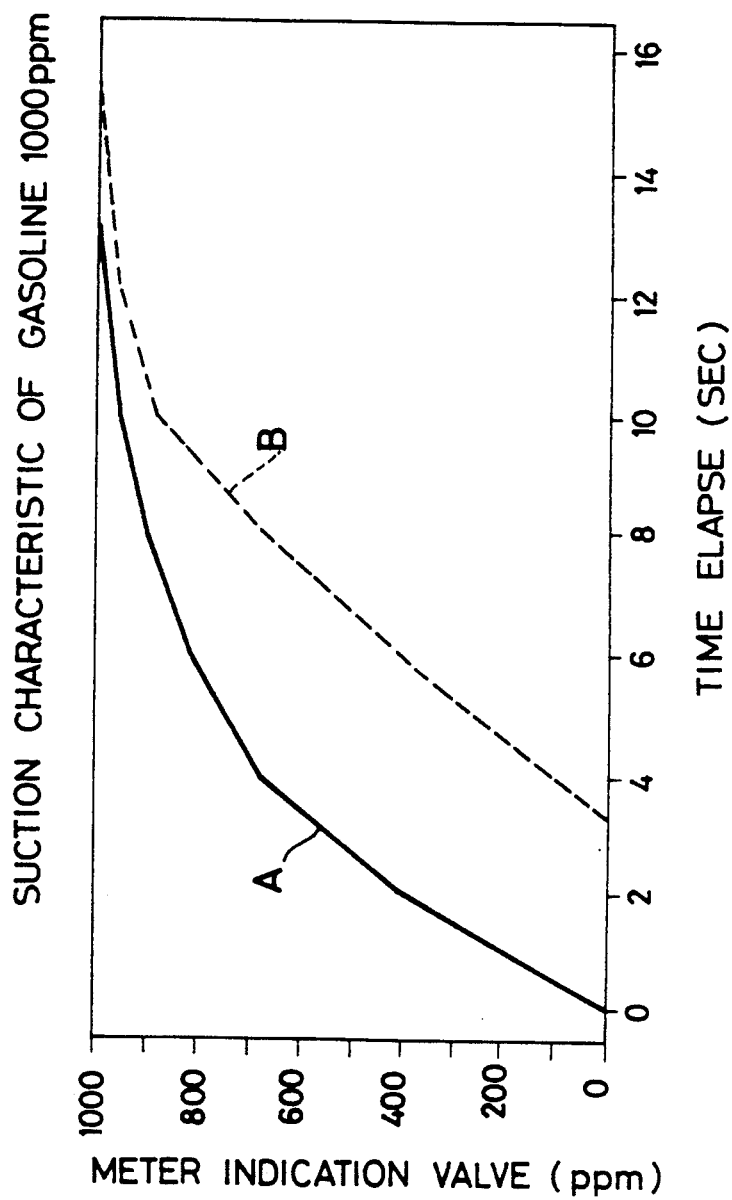

GASOLINE DETECTING DEVICE

BACKGROUND OF THE INVENTION

The present invention relates gasoline detecting device which can improve a detecting speed of a gasoline detecting device, suitable for inspection of gasoline leakage from an engine or the like.

Generally, in a gasoline engine for a vehicle or the like, inspection of gasoline leakage is executed after assembling of the vehicle.

The inspection is arranged such that air adjacent to the engine is sucked, existence of gasoline in the air is investigated, and it is judged whether or not the gasoline leaks.

A potable or handy gas detector and a concentration meter are known as an detecting device of suction type used in the above-described inspection, in which a pump is used to execute sampling of gas, to measure concentration of the gas, and the like.

An example of the inspecting device will briefly be described. A suction nozzle is mounted adjacent to an engine to be inspected, and a body is arranged at a location spaced from the engine. The suction nozzle and the body are connected to each other by a spaced-portion connecting pipe or the like for leading the sucked air.

A sensor, sensor driving means for driving the sensor and for displaying inspected results, a pump and the like are arranged within the body.

When the air sucked by the pump flows into the body section through the spaced-portion connecting pipe, existence of leakage is displayed depending upon existence of gasoline detected by the sensor.

In the suction type detecting device of the kind referred to above, the body must be arranged within atmosphere different from that of a measuring location. For this reason, a distance from the suction nozzle to the sensor increases so that it is inevitable that the detecting speed is remarkably slowed.

On the other hand, it has been tried to execute such inspection on a manufacturing line. However, the conventional detecting device has the following disadvantages. That is, there are a plurality of measuring locations, and it is required to execute measurement at a single location in short time such as 2 to 3 sec. The conventional detecting device which is slow in detecting speed as described above cannot fulfill such requirement.

As described above, the conventional gasoline detecting device has such disadvantages that the detecting speed is slow, and it is impossible to efficiently execute inspection of gasoline leakage from the element to be inspected.

SUMMARY OF THE INVENTION

It is therefore an object of the invention to provide a gasoline detecting device which is fast in detecting speed, and which can inspect gasoline leakage highly efficiently.

According to the invention, there is provided a gasoline detecting device for detecting gasoline leakage from an element to be inspected, the gasoline detecting device comprising:
 a suction nozzle for sucking air, arranged adjacent to the element to be inspected;
 a sensor for detecting gasoline within the sucked air, arranged adjacent to the suction nozzle; and
 a body arranged in relation spaced from the suction nozzle, said body having sensor drive means for driving the sensor and for displaying the detected data and suction means communicating with the nozzle.

As describe above in detail, the gasoline detecting device according to the invention has the sensor which is arranged adjacent to the suction nozzle. Accordingly, response time from start of the measurement is short, and the detecting speed is extremely fast. Thus, it is possible to inspect leakage with high efficiency. Inspection on a manufacturing line is also possible.

BRIEF DESCRIPTION OF THE DRAWINGS

FIG. 4 is a view showing characteristic curves, for comparison between the characteristic of the detecting device of the invention, illustrated in FIG. 1, and a characteristic of a conventional detecting device.

DETAILED DESCRIPTION OF THE PREFERRED EMBODIMENT

An embodiment of the invention will hereunder be described in detail with reference to the accompanying drawings.

Figure 1:
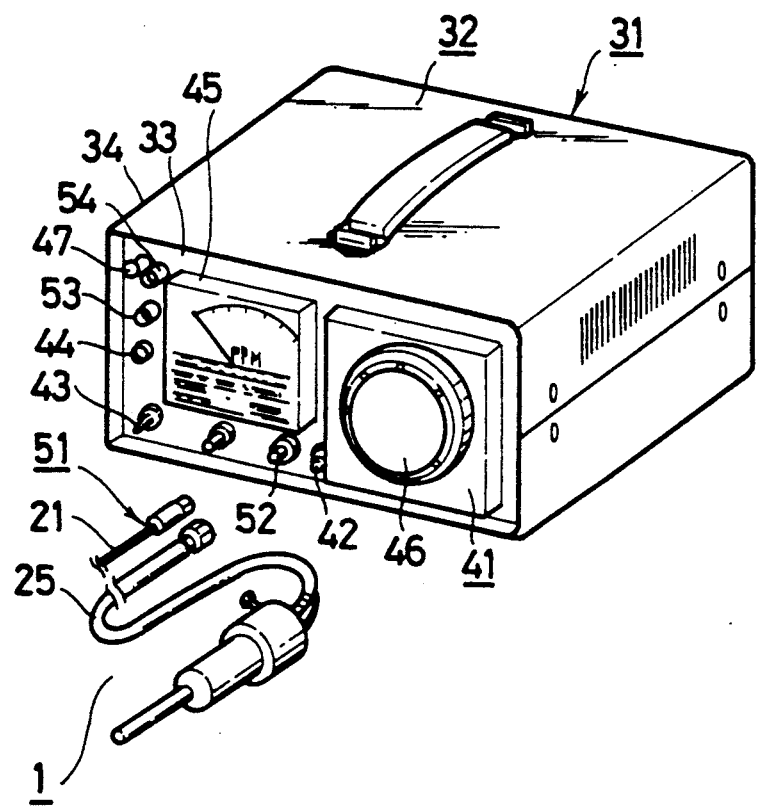
FIG. 1 is a perspective view showing an entire arrangement of a gasoline detecting device according to an embodiment of the invention.

Referring first to FIG. 1, there is shown, in a perspective view, an entire arrangement of a gasoline detecting device according to the invention, which is provided with a nozzle section 1 and a body section 31.

Figure 2:
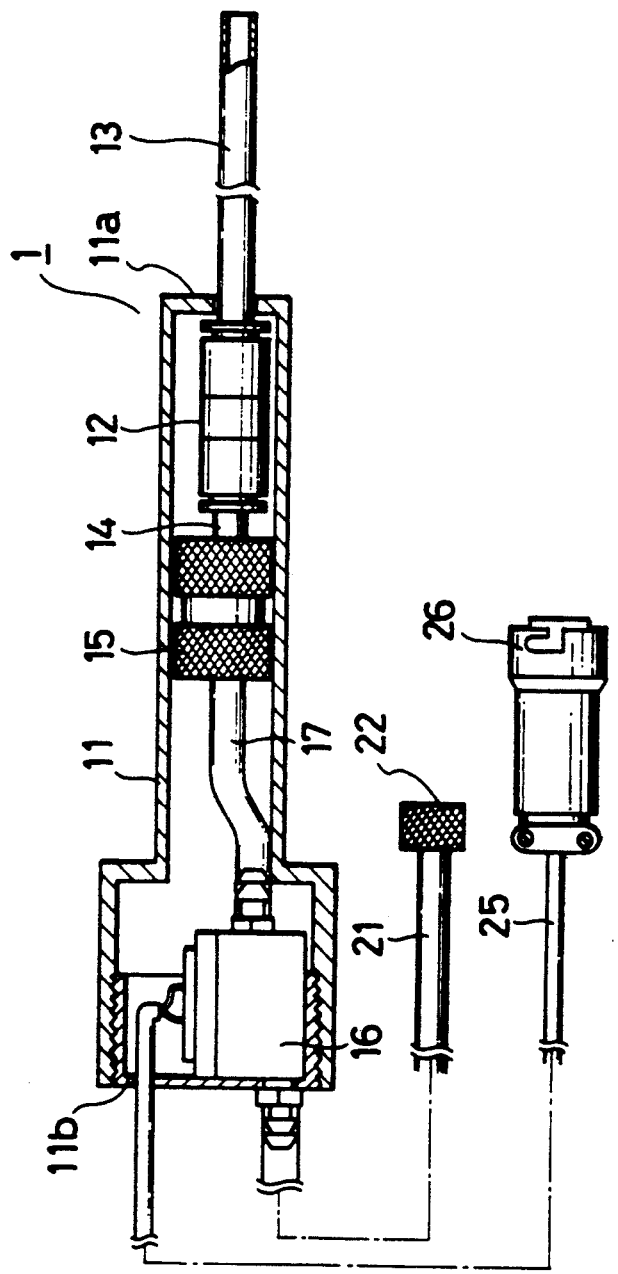
FIG. 2 is a cross-sectional view showing a suction nozzle section of the arrangement illustrated in FIG. 1.

As shown in FIG. 2, the nozzle section 1 is provided with a sensor housing 11 including a tubular element having a bottom, which has a smaller diameter portion and a larger diameter portion. The smaller diameter portion has one end thereof which serves as a closed end 11a having a through bore, while a cup-like closure or lid 11b having through bores is detachably screwed into one end of the larger diameter portion so that the one end of the larger diameter portion is closed.

Further, a coupling 12 is received in the smaller diameter portion adjacent to the one end thereof. A suction nozzle 13 for sucking air consisting of a flexible pipe is connected to one end of the coupling 12 and extends through the through bore in the closed end 11a so as to project from the sensor housing 11. Moreover, a drain pot 15 is connected to the other end of the coupling 12 through a connection hose 14.

On the other hand, a sensor 16 for detecting gasoline within sucked air is mounted adjacent to the one end of the larger diameter portion. The sensor 16 has one end thereof which is connected to the drain pot 15 through a connection hose 17 such that air can flow therebetween.

Furthermore, a connecting hose consisting of a vinyl tube serving as a spaced-portion connecting pipe 21 is fitted in the other end of the sensor 16. The connecting pipe 21 extends through the through bore in the closure 11b, and has a tip thereof on which a hose connector 22 for connection to the body section 31 is mounted.

Further, a lead wire (four-core shield wire) 25 having four wire elements for power source and detection extends from the sensor 16 through the closure 11b. The lead wire 25 has a forward end thereof on which a 4P sensor power-source connector 26 is mounted.

Air is capable of flowing from the suction nozzle 13 to the hose connector 22 through the coupling 12, the drain pot 15, the sensor 16 and the spaced-portion connecting hose 21.

The body section 31 has a body 32. The body 32 has a box 34, sensor drive means 41 and suction means 51.

The box 34 is a box-like element having, at a front face thereof, a display panel 33. The above-described various elements 41, 51 are received within the box 34. A display element, an operating element and the like are mounted on the panel 33.

The sensor drive means 41 comprises a sensor drive circuit (not shown) received in the box 34, a connector 42 into which the sensor power-source connector 26 mounted on the panel 33 is fitted, a power switch 43, an operation lamp 44, a meter 45 for displaying concentration of the gasoline, an alarm buzzer 46 for informing leakage of the gasoline, an alarm lamp 47 for informing leakage, and the like.

The suction means 51 comprises a suction pump (not shown) received in the box 34, a nozzle connecting port 52 for connection of the connecting hose 21, a lamp 53 for judging abnormality of a flow speed, a flow-speed alarm lamp 54, and the like.

Operation of the embodiment will next be described.

Figure 3:
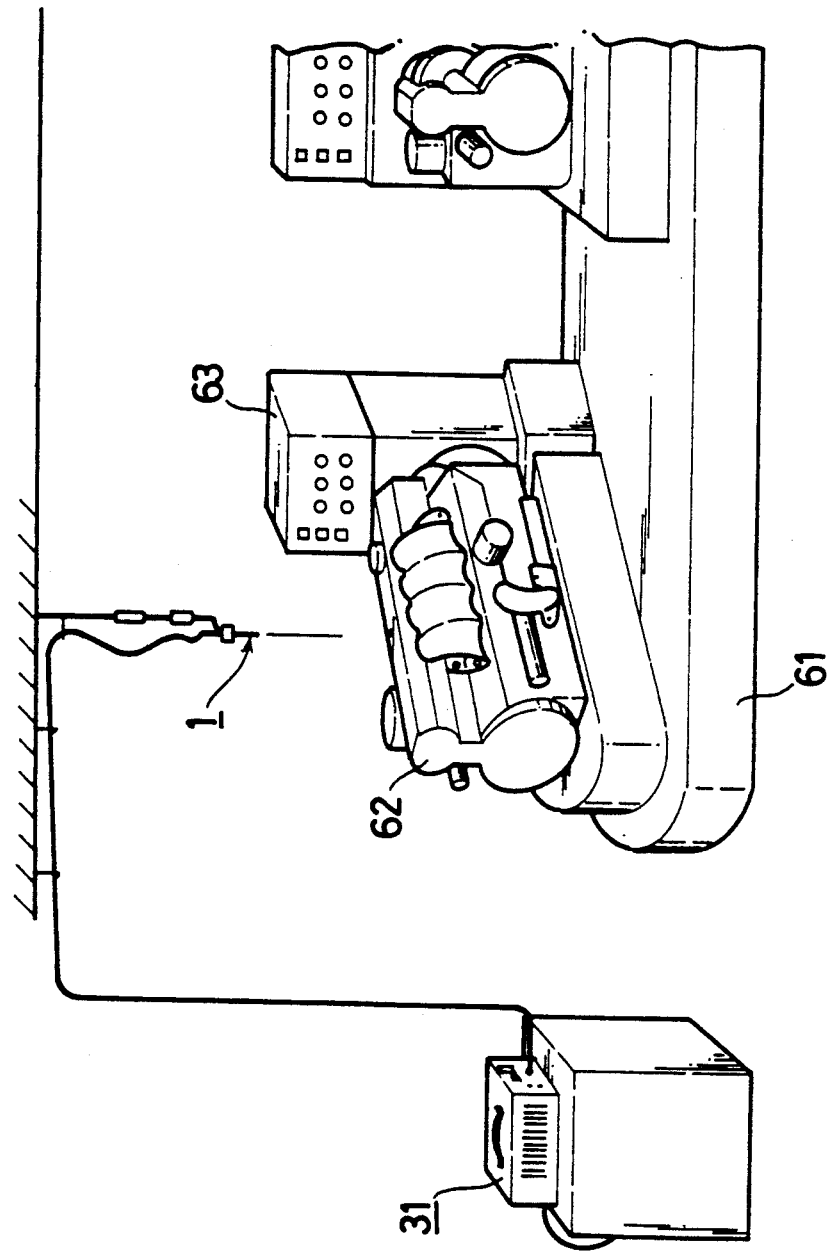
FIG. 3 is a perspective view for description of a function, showing an inspecting condition of the arrangement illustrated in FIG. 1.

FIG. 3 is a view showing how the detecting device according to the invention is arranged at inspection. An engine 62 as an element to be inspected is mounted on a turn table 61 for inspection of the engine. An inspecting unit 63 for the engine is mounted on a location behind the engine. The nozzle section 1 and the body section 31 of the gasoline detecting device are arranged in relation spaced from each other a predetermined interval.

Further, FIG. 4 is a view for comparison in characteristic between the detecting device according to the invention and the conventional detecting device. The abscissa indicates elapsed time from start of measurement, while the ordinate indicates an indication value of the concentration display meter 45.

Now, when the power switch 43 is turned on, the operation lamp 44 is turned on. The pump starts to rotate so that suction of air starts. It is confirmed that fluid flows at a normal speed.

Then, as the nozzle section 1 is confronted with or faces against a location adjacent to a part of the engine 62 to be inspected in gasoline leakage, sucked air passes through the coupling 12 and the drain pot 15, and passes through the sensor 16. The sucked air reaches the pump through the spaced-portion connecting hose 21, and is discharged. During the passage, when the sensor 16 detects gasoline, if the display on the concentration display meter 45 is equal to or more than a predetermined value, for example, the alarm buzzer 46 is turned on, and the leakage alarm lamp 47 is also turned on. Thus, it is judged that the gasoline leaks.

If there is no leakage, the suction nozzle 13 is moved to a next measuring position.

As described above, since the sensor 16 is arranged adjacent to the nozzle 13, detection starts simultaneously with suction.

Operation in case where the gasoline is contained 1000 ppm will be described with reference to the diagram illustrated in FIG. 4.

In FIG. 4, the solid line A indicates a characteristic of the present embodiment, while the broken line B indicates a characteristic of the conventional detecting device. As will be clear from FIG. 4, the arrangement of the embodiment according to the invention in which the sensor 16 is arranged adjacent to the suction nozzle 13 has almost no time lag from start of the measurement to start of the detection, whereas the conventional arrangement has time lag of about 3 sec.

On the other hand, in case where inspection is practically executed on a manufacturing line, it is sufficient if existence of the leakage can be judged, without investigation or inspection of the concentration. Accordingly, judgment of the leakage inspection is sufficiently possible by response of 2 sec to 3 sec which indicates 30% to 40%.

In connection with the above, in an improvement of the response speed, further advantage can be expected by the fact that an internal volume of each of the drain pot and the spaced-portion connecting hose is reduced, in addition to the position of the sensor.

The description of the present embodiment will be completed as described above. In the present embodiment, the gasoline engine has been described as an element to be inspected. However, the invention should not be limited to this arrangement. The invention may be applied to another inspection of gasoline leakage.

Further, spacing between the suction nozzle and the body section may be set depending upon the atmosphere.

What is claimed is:

1. A gasoline detecting device for detecting gasoline leakage from an element to be inspected, said gasoline detecting device comprising:

a suction nozzle for drawing an air sample from the element to be inspected, having first and second ends, said first end thereof being arranged adjacent to the element to be inspected;

a sensor for detecting gasoline within the air sample, arranged adjacent to the second end of said suction nozzle;

a body arranged in spaced relation from said suction nozzle, said body having sensor drive means for driving said sensor and for displaying the detected data, and further including suction means communicating with the second end of said suction nozzle;

a sensor housing for receiving said sensor, having first and second ends thereof, the second end of said suction nozzle being mounted on the first end of said sensor housing such that said suction nozzle extends from the first end of said sensor housing;

a coupling arranged within said sensor housing at a location adjacent to the first end of said sensor housing;

a drain pot arranged between said coupling and said sensor;

a first connecting hose having first and second ends, said first end thereof being connected to said coupling, the second end of said first connecting hose being connected to said drain pot; and a second connecting hose having first and second ends, said first end thereof being connected to said drain pot, the second end of said second connecting hose being connected to said sensor.

2. A gasoline detecting device according to claim 1, wherein said sensor housing has a smaller diameter portion and a larger diameter portion connected thereto, said coupling, said first and second connecting hoses and said drain pot being arranged within said smaller diameter portion of said sensor housing, said sensor being arranged within said larger diameter portion of said sensor housing.

3. A gasoline detecting device for detecting gasoline leakage from an element to be inspected, said gasoline detecting device comprising;
- a suction nozzle for drawing an air sample from the element to be inspected, having first and second ends, said first end thereof being arranged adjacent to the element to be inspected;
- a sensor for detecting gasoline within the air sample, arranged adjacent to the second end of said suction nozzle;
- a body arranged in spaced relation from said suction nozzle, said body having sensor drive means for driving said sensor and for displaying the detected data, and further including suction means communicating with the second end of said suction nozzle;
- a sensor housing for receiving said sensor, having first and second ends thereof, the second end of said suction nozzle being mounted on the first end of said sensor housing such that said suction nozzle extends from the first end of said sensor housing, and further including an end wall adjacent said second end of said sensor housing;
- a connecting hose extending through said end wall of said sensor housing, said connecting hose having first and second ends, said first end thereof being connected to said sensor; and
- a hose connector adapted to be connected to said body, the second end of said connecting hose being connected to said hose connector.

* * * * *